United States Patent
Lepaih

Patent Number: 5,954,768
Date of Patent: Sep. 21, 1999

[54] PROCESS FOR THE MANUFACTURE OF PROSTHETIC IMPLANTS

[75] Inventor: Alain Lepaih, Thaon, France

[73] Assignee: Benoist Girard & Cie, France

[21] Appl. No.: 08/926,280

[22] Filed: Sep. 5, 1997

[51] Int. Cl.[6] .............................. A61F 2/28; A61F 2/30; B23K 1/00; B22F 1/04

[52] U.S. Cl. .............................. 623/16; 623/11; 623/18; 228/101; 419/2

[58] Field of Search .............................. 623/16, 11, 18, 623/66; 228/101; 419/2

[56] References Cited

U.S. PATENT DOCUMENTS 4,355,428  10/1982  Deloison et al. .

Primary Examiner—Mickey Yu
Assistant Examiner—Dinh X. Nguyen
Attorney, Agent, or Firm—Lerner, David, Littenberg, Krumholz & Mentlik, LLP

[57] ABSTRACT

A process for the manufacture of prosthetic implants with a roughened tissue ingrowth surface consists in obtaining an even surface roughening in the form of balls in which the balls made integral with the implant all have the same diameter and have been obtained by uniformly distributing the balls through a mesh onto the surface to be roughened. Such implants have fewer risks after implantation because the bony tissue ingrowth is on a more uniform surface.

9 Claims, 3 Drawing Sheets

PROCESS FOR THE MANUFACTURE OF PROSTHETIC IMPLANTS

BACKGROUND OF THE INVENTION

1. Field of the Invention

The subject of the present invention is a process for the manufacture of implants or prosthetic elements with an even madreporic surface (i.e., a surface roughened by small balls). This surface has part spherical protuberances formed during the casting process.

2. Description of the Prior Art

Surgical prostheses, particularly those for joint articulation, such as those of the knee or hip, are usually implanted on or in broken bones, the parts thereof which are in a deteriorated condition having been removed with a surgical saw.

It is essential, with this type of implanted prostheses, that the prosthetic parts in contact with the resected parts of the bone which is in good condition, can be integrated into the bone in the process of reconstitution such as by the ingrowth of bone tissue.

To achieve this end, it is already known how to resort to implants made of material compatible with the bones and how to provide that the surfaces of these implants facilitate the implantation of the bony tissue undergoing regeneration.

It has thus been proposed, for example in the applicant's U.S. Pat. No. 4,355,428, the teachings of which are incorporated herein by reference, that the surfaces of these implants be rendered madreporic, i.e., that they be constituted by a multitude of small balls, all of which form an integral part with the generally metallic material constituting the prosthetic implant itself.

In the process of the '428 patent, prior to casting using the lost wax technique, meltable balls, which generally have a certain range of diameter, are sprinkled on the surface of a wax model of the implant precoated with glue.

During such sprinkling, the greater possible heterogeneity of the surface is favored by using balls of the same diameter or different diameters and distributing them, generally by hand, in an uneven manner so as to increase as much as possible the intervals, crevices or interstices between neighboring balls, in order to promote the ingrowth and development of the bone fibrils being reformed after implantation of the prosthesis.

The wax prosthesis model thus obtained is covered by ceramic which makes possible the production of a female mold of refractory material into which, after melting of the wax and balls—hence the name "lost wax process"—the metal or alloy constituting the prosthesis can be poured and the corresponding prosthesis with the sought-after surface appearance obtained.

It was found, however, that such a production process for prostheses, already burdensome because it requires the preparation of a wax model for each prosthesis to be made, was very much dependent on the operator doing the manual sprinkling, gluing, and fixation of the balls on the wax model. This results in prostheses whose surface appearance exhibits the desired irregularities, but whose order of magnitude varies considerably from one prosthesis to the next and did not reliably allow for their identical reproduction.

SUMMARY OF THE INVENTION

The object of the present invention is to improve the manufacture of the madreporic surfaces of such prostheses by freeing them from the hazards of surface irregularities linked to the manipulation of the meltable balls by an operator, while ensuring a regular distribution of the balls over the entire surface to be rendered madreporic and proportionately reducing the number of rejects.

To achieve this end, the process according to the present invention consists in the conventional process for the manufacture of prosthetic implants having a madreporic surface in accordance with the lost wax method, uniformly distributing the balls on the glue-covered surface to be coated in a perfectly homogeneous manner by means of a grid whose meshes correspond to the dimensions of the balls and whose dimensions correspond to those of the surface to be coated.

The choice of a grid held at a suitable distance from the surface to be coated, generally corresponding to the diameter of one ball, and the meshes of which are determined so as to allow a single ball to pass through without friction makes it possible to obtain an even distribution of the balls on the glue-coated surface of the wax model of the implant.

Moreover, the selection of a single dimension for all the balls, obviously corresponding to the individual passage of a single ball per mesh through the grid without friction, makes it possible to obtain a geometric distribution of the balls rigorously corresponding to the meshwork of the grid.

The uniform distribution of the balls of the same size over the entire surface of the implant renders this madreporic surface in contact with the bone environment to be reconstructed perfectly homogeneous and even, without the presence of any points on the prosthesis where tissue attaches to strongly or where no tissue attaches, which, because of their unpredictable irregularity, can cause imbalance points in the implantation of the prosthesis, with all the resulting risks of rupture.

Such an improvement makes the prosthesis thus obtained more reliable as a result of the improvement in the conditions of implantation into the bone undergoing reconstitution; the prosthesis obtained according to the process of the invention are therefore also part of the present invention.

The manufacturing process according to the invention includes the following stages:

- manufacturing by the conventional method of a prosthesis implant model using the lost wax method;
- coating the surface of the part to be roughened or rendered madreporic with glue;
- positioning a perforated grid, the dimensions and shape of which conform to those of the surface to be rendered madreporic and the meshes or perforations of which correspond to the diameter of the balls;
- sprinkling the entire surface of the grid of the implant with meltable balls, generally made of wax or polystyrene, having a diameter appropriate to the perforations of the grid and to the state of the surface one wishes to obtain;
- constructing a mold made of refractory material around the piece of wax, some of whose glue-coated surfaces are covered by a uniform layer of balls;
- melting the wax and balls in the autoclave;
- casting the alloy or metal constituting the implant in the refractory mold;
- and breaking up this refractory mold in order to recover the implant from it in a single piece having the madreporic surface according to the invention.

The material constituting the prosthetic implants must be a material capable of being cast in a foundry and suitable for bone implants, i.e., essentially metal alloys such as chromium-cobalt alloys, stainless steel, titanium alloys, and, depending on the circumstances, thermoplastic materials.

The prosthetic implants refer to all surgical prostheses used in human surgery, notably for joint articulations, among which hip prostheses and knee prostheses are the most widespread.

Only certain surfaces, in particular one or several plane elements of such prostheses, can be rendered madreporic according to the process of the present invention.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
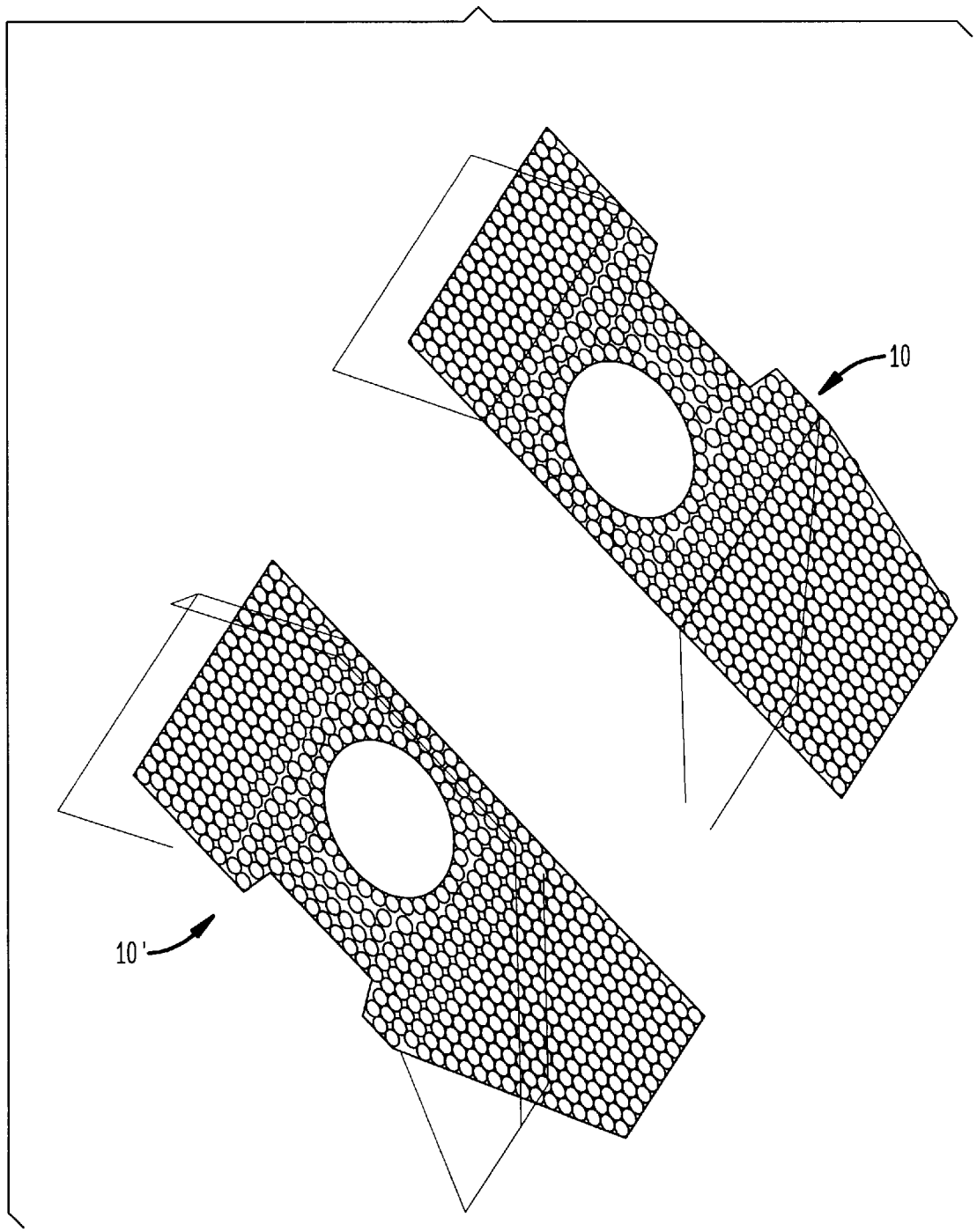
FIG. 1 is a perspective view of a mesh designed to be used with the femoral component of a knee.

Referring to FIG. 1 there is shown a perspective view of a mesh (10, 10') for use on the internal surface of a femoral element of a knee prosthesis, on which it will be noted that both the right and left sides of such mesh present three different plane surfaces which are used to render the inner surface of a femoral prosthesis madreporic by the process according to the invention by using meltable balls of the same diameter. It should be noted in this regard that in any prosthetic element the surface to be rendered madreporic can be plane or not and that several of the prostheses surfaces can become madreporic with a coating of balls of identical diameter for each surface. In addition, the diameter of the balls may vary from one surface to the next; in fact, one need only apply a suitably sized grid to each surface.

Figure 2:
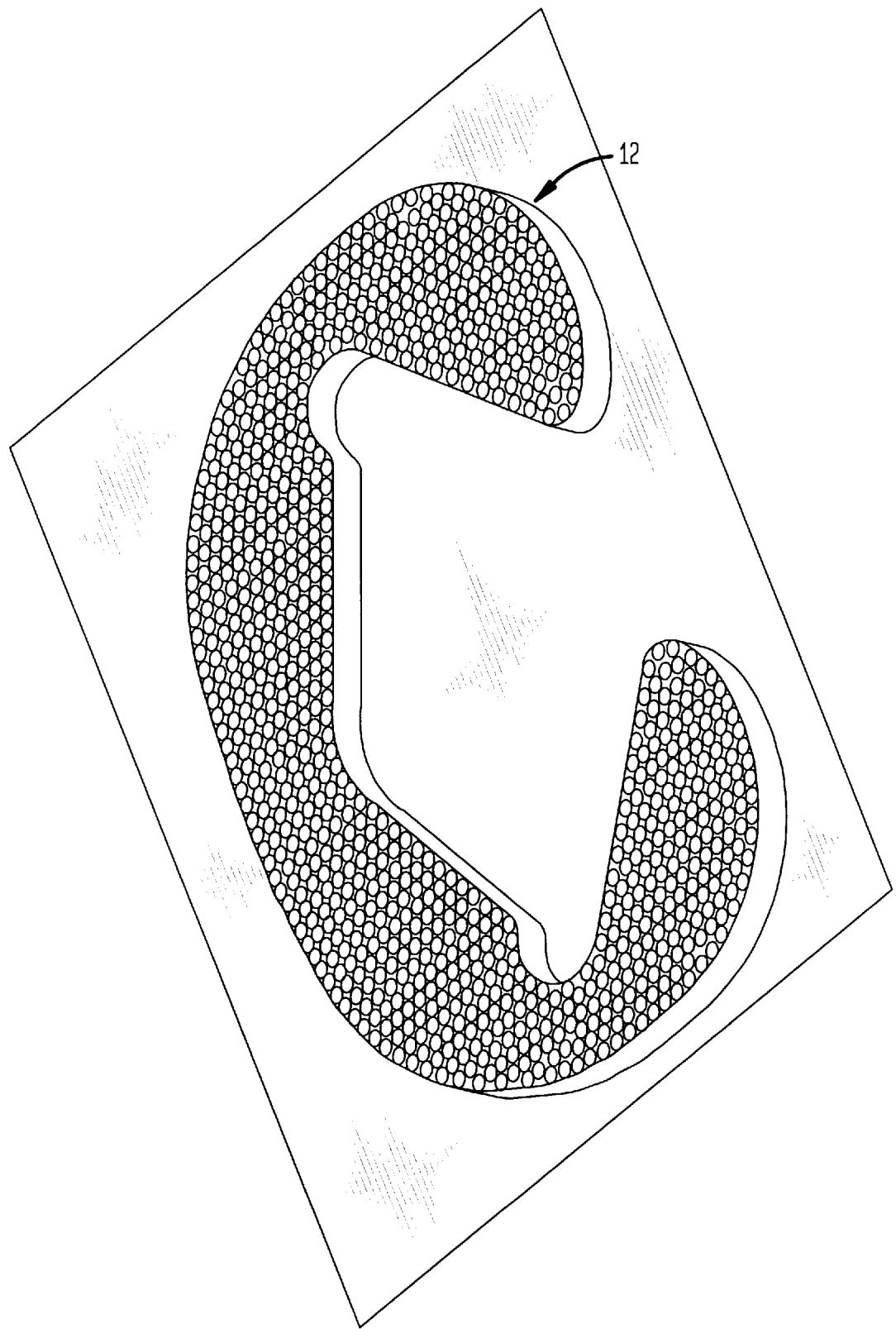
FIG. 2 is a perspective view of a tibial component formed by a suitably shaped mesh.

Referring to FIG. 2, there is shown a perspective view of the inner part of a tibial element 12 of a knee prosthesis, where we see that the entire lower surface, which is in contact with the resected part of the upper part of the tibia, has been coated with a uniform madreporic coating according to the process of the invention.

The grid (10, 10'), used for carry out the invention, can consist of a square meshwork, each mesh side of which is slightly greater than the diameter of one ball, in order to allow one ball to pass through without friction (for example, sides of 0.8 mm square for a ball of 0.75 mm in diameter).

Figure 3:
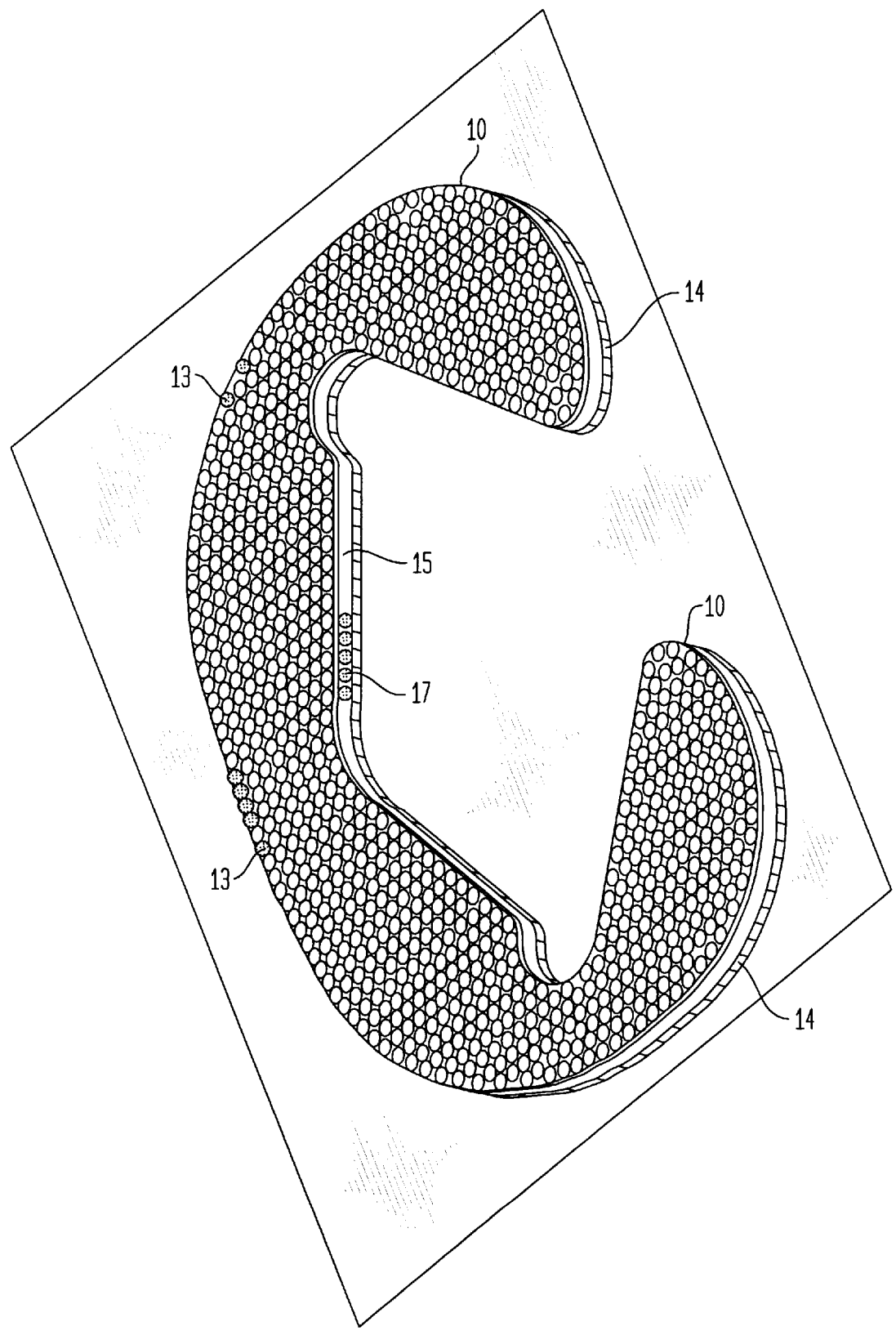
FIG. 3 is a perspective view of a mesh placed close to a meltable implant model with several meltable balls placed above the mesh and on the surface of the model.

The grid (10, 10') may be held very close or placed on the wax model of the prosthesis. The balls then bond to the wax base and are coated by ceramic as described above. FIG. 3 shows a wax model of a tibial baseplate 14 with a mesh 10 spaced close to the top 15 of baseplate 14. Meltable balls 13 are shown placed on the openings of mesh 10. Balls 17 are shown glued to surface 15 after passing through the openings in the mesh. Since the mesh 10 is placed close to or on the surface 15, only one layer of meltable balls are placed on model 14 prior to coating and casting.

It can also consist of a plate with square or round apertures, the dimensions of which are likewise calculated to allow one ball to pass through without friction.

The balls are generally made of thermoplastic material, preferably polystyrene; they have a diameter ranging from 0.3 to 2 mm.

These balls are glued to the surface of the implant to be rendered madreporic by any means of fixation known to those skilled in the art.

The present invention may be subject to changes and the scope of the protection sought is defined by the set of claims which follow.

I claim:

1. A process for the manufacture of an ingrowth surface for a prosthetic implant comprising the steps of:

coating the surface of a meltable model of the implant with glue;

positioning a mesh immediately adjacent said surface;

evenly distributing meltable balls of a generally uniform diameter onto said surface of the meltable model by sprinkling said balls on said mesh, having openings whose size corresponds to the diameter of a desired ball size, said mesh having a shape generally corresponding to the surface to be coated;

constructing a mold made of refractory material around the ball coated model;

melting the meltable model and balls and removing this melted material from the mold; and casting a metal in the mold and breaking up the mold to obtain an implant with a uniform roughened surface.

2. The process as set forth in claim 1 wherein the balls are made of polystyrene.

3. The process according to claim 1 wherein the diameter of the balls is between 0.3 and 2 mm.

4. The process according to claim 1 wherein the implant is an element of a prosthetic joint.

5. The process according to claim 4, wherein the roughened surface is in contact with the resected part of the corresponding bone of the joint.

6. The process according to claim 1 wherein the mesh consists of square openings sized to allow one ball to pass through without friction.

7. The process according to claim 1 wherein the mesh consists of a plate with square or round apertures allowing one ball to pass through without friction.

8. A prosthetic implant manufactured by the process of claim 1 wherein at least one surface of which is roughened and is in the form of balls integral with the implant itself and uniformly distributed in a perfectly homogeneous manner.

9. The implant according to claim 8, wherein said implant is made of a castable metallic material.

* * * * *

UNITED STATES PATENT AND TRADEMARK OFFICE
CERTIFICATE OF CORRECTION

PATENT NO. : 5,954,768
DATED : September 21, 1999
INVENTOR(S) : Lepaih It is certified that error appears in the above-identified patent and that said Letters Patent is hereby corrected as shown below:

Column 4, line 27, after the "," insert -- said mesh --.

Signed and Sealed this

First Day of May, 2001

*Attest:*

NICHOLAS P. GODICI

*Attesting Officer*   *Acting Director of the United States Patent and Trademark Office*